United States Patent
Oldham-Haltom et al.

(10) Patent No.: US 11,499,179 B2
(45) Date of Patent: *Nov. 15, 2022

(54) REAL TIME CLEAVAGE ASSAY

(71) Applicant: EXACT SCIENCES DEVELOPMENT COMPANY, LLC, Madison, WI (US)

(72) Inventors: Rebecca Oldham-Haltom, Marshall, WI (US); Hongzhi Zou, Middleton, WI (US); Graham P. Lidgard, Madison, WI (US); Michael J. Domanico, Middleton, WI (US); Hatim Allawi, Middleton, WI (US)

(73) Assignee: Exact Sciences Development Company, LLC, Madison, WI (US)

( * ) Notice: Subject to any disclaimer, the term of this patent is extended or adjusted under 35 U.S.C. 154(b) by 258 days.

This patent is subject to a terminal disclaimer.

(21) Appl. No.: 16/789,276

(22) Filed: Feb. 12, 2020

(65) Prior Publication Data

US 2020/0248245 A1    Aug. 6, 2020

Related U.S. Application Data

(63) Continuation of application No. 15/068,364, filed on Mar. 11, 2016, now Pat. No. 10,604,793, which is a continuation of application No. 15/019,758, filed on Feb. 9, 2016, now abandoned, which is a continuation of application No. 13/720,757, filed on Dec. 19, 2012, now Pat. No. 9,290,797, which is a continuation of application No. 12/946,737, filed on Nov. 15, 2010, now Pat. No. 8,361,720.

(51) Int. Cl.
| | |
|---|---|
| *C12Q 1/68* | (2018.01) |
| *C12Q 1/6827* | (2018.01) |
| *C12Q 1/686* | (2018.01) |
| *C12Q 1/6818* | (2018.01) |
| *C12Q 1/6886* | (2018.01) |

(52) U.S. Cl.
CPC ......... *C12Q 1/6827* (2013.01); *C12Q 1/686* (2013.01); *C12Q 1/6818* (2013.01); *C12Q 1/6886* (2013.01); *C12Q 2600/156* (2013.01); *C12Q 2600/158* (2013.01)

(58) Field of Classification Search
CPC .............................. C12Q 1/686; C12Q 1/6818
See application file for complete search history.

(56) References Cited

U.S. PATENT DOCUMENTS

| | | |
|---|---|---|
| 5,541,311 A | 7/1996 | Dahlberg et al. |
| 5,614,402 A | 3/1997 | Dahlberg et al. |
| 5,719,028 A | 2/1998 | Dahlberg et al. |
| 5,795,763 A | 8/1998 | Dahlberg et al. |
| 5,837,450 A | 11/1998 | Dahlberg et al. |
| 5,843,654 A | 12/1998 | Heisler et al. |
| 5,843,669 A | 12/1998 | Kaiser et al. |
| 5,846,717 A | 12/1998 | Brow et al. |
| 5,874,283 A | 2/1999 | Harrington et al. |
| 5,888,780 A | 3/1999 | Dahlberg et al. |
| 5,985,557 A | 11/1999 | Prudent et al. |
| 5,994,069 A | 11/1999 | Hall et al. |
| 6,001,567 A | 12/1999 | Brow et al. |
| 6,090,543 A | 7/2000 | Prudent et al. |
| 6,090,606 A | 7/2000 | Kaiser et al. |
| 6,194,149 B1 | 2/2001 | Neri et al. |
| 6,210,880 B1 | 4/2001 | Lyamichev et al. |
| 6,214,545 B1 | 4/2001 | Dong et al. |
| 6,348,314 B1 | 2/2002 | Prudent et al. |
| 6,355,437 B1 | 3/2002 | Neri et al. |
| 6,358,691 B1 | 3/2002 | Neri et al. |
| 6,372,424 B1 | 4/2002 | Brow et al. |
| 6,458,535 B1 | 10/2002 | Hall et al. |
| 6,555,357 B1 | 4/2003 | Kaiser et al. |
| 6,562,611 B1 | 5/2003 | Kaiser et al. |
| 6,635,463 B2 | 10/2003 | Ma et al. |
| 6,673,616 B1 | 1/2004 | Dahlberg et al. |
| 6,692,917 B2 | 2/2004 | Neri et al. |
| 6,706,471 B1 | 3/2004 | Brow et al. |
| 6,709,815 B1 | 3/2004 | Dong et al. |

(Continued)

FOREIGN PATENT DOCUMENTS

| | | | |
|---|---|---|---|
| WO | WO2009155271 | 12/2009 | |
| WO | WO-2012067831 A1 * | 5/2012 | ........... C12Q 1/6827 |

OTHER PUBLICATIONS

Tadokoro, K., Kobayashi, M., Yamaguchi, T., Suzuki, F., Miyauchi, S., Egashira, T. and Kumada, H., 2006. Classification of hepatitis B virus genotypes by the PCR-Invader method with genotype-specific probes. Journal of Virological methods, 138(1-2), pp. 30-39. (Year: 2006).*

(Continued)

*Primary Examiner* — Teresa E Strzelecka
*Assistant Examiner* — Olayinka A Oyeyemi
(74) *Attorney, Agent, or Firm* — Bozicevic, Field & Francis LLP; Shweta Chandra

(57) ABSTRACT

A cleavage-based real-time PCR assay method is provided. In general terms, the assay method includes subjecting a reaction mixture comprising a) PCR reagents for amplifying a nucleic acid target, and b) flap cleavage reagents for performing a flap cleavage assay on the amplified nucleic acid target to two sets of thermocycling conditions. No additional reagents are added to the reaction between said first and second sets of cycles and, in each cycle of the second set of cycles, cleavage of a flap probe is measured.

14 Claims, 3 Drawing Sheets

Specification includes a Sequence Listing.

(56) References Cited

U.S. PATENT DOCUMENTS

| | | | |
|---|---|---|---|
| 6,709,819 B2 | 3/2004 | Lyamichev et al. | |
| 6,759,226 B1 | 7/2004 | Ma et al. | |
| 6,780,585 B1 | 8/2004 | Dong et al. | |
| 6,780,982 B2 | 8/2004 | Lyamichev et al. | |
| 6,872,816 B1 | 3/2005 | Hall et al. | |
| 6,875,572 B2 | 4/2005 | Prudent et al. | |
| 6,913,881 B1 | 7/2005 | Aizenstein et al. | |
| 6,932,943 B1 | 8/2005 | Cracauer et al. | |
| 7,011,944 B2 | 3/2006 | Prudent et al. | |
| 7,045,289 B2 | 5/2006 | Allawi et al. | |
| 7,060,436 B2 | 6/2006 | Lyamichev et al. | |
| 7,067,643 B2 | 6/2006 | Dahlberg et al. | |
| 7,087,381 B2 | 8/2006 | Dahlberg et al. | |
| 7,101,672 B2 | 9/2006 | Dong et al. | |
| 7,122,364 B1 * | 10/2006 | Lyamichev | C12N 9/22 |
| | | | 435/199 |
| 7,150,982 B2 | 12/2006 | Allawi et al. | |
| 7,195,871 B2 | 3/2007 | Lyamichev et al. | |
| 7,256,020 B2 | 8/2007 | Lyamichev et al. | |
| 7,273,696 B2 | 9/2007 | Dahlberg et al. | |
| 7,297,780 B2 | 11/2007 | Skrzypczynski et al. | |
| 7,306,917 B2 | 12/2007 | Prudent et al. | |
| 7,312,033 B2 | 12/2007 | Accola et al. | |
| 7,354,708 B2 | 4/2008 | Hall et al. | |
| 7,381,530 B2 | 6/2008 | Hall et al. | |
| 7,384,746 B2 | 6/2008 | Lyamichev et al. | |
| 7,407,782 B2 | 8/2008 | Prudent et al. | |
| 7,429,455 B2 | 9/2008 | Dong et al. | |
| 7,432,048 B2 | 10/2008 | Neri et al. | |
| 7,435,390 B2 | 10/2008 | Cracauer et al. | |
| 7,462,451 B2 | 12/2008 | Skrzypczynski et al. | |
| 7,473,773 B2 | 1/2009 | Elagin et al. | |
| 7,482,118 B2 | 1/2009 | Allawi et al. | |
| 7,482,127 B2 | 1/2009 | Agarwal et al. | |
| 7,514,220 B2 | 4/2009 | Hall et al. | |
| 7,527,928 B2 | 5/2009 | Neri et al. | |
| 7,527,948 B2 | 5/2009 | Hudson et al. | |
| 7,541,145 B2 | 6/2009 | Prudent et al. | |
| 7,582,436 B2 | 9/2009 | Hall et al. | |
| 7,588,891 B2 | 9/2009 | Prudent et al. | |
| 7,601,496 B2 | 10/2009 | Dahlberg et al. | |
| 7,674,924 B2 | 3/2010 | Skrzypczynski et al. | |
| 7,678,542 B2 | 3/2010 | Lyamichev et al. | |
| 7,691,573 B2 | 4/2010 | Dahlberg et al. | |
| 7,700,750 B2 | 4/2010 | Mast et al. | |
| 8,361,720 B2 * | 1/2013 | Oldham-Haltom | C12Q 1/686 |
| | | | 435/6.1 |
| 8,916,344 B2 | 12/2014 | Zou et al. | |
| 9,290,797 B2 * | 3/2016 | Oldham-Haltom | C12Q 1/686 |
| 10,604,793 B2 * | 3/2020 | Oldham-Haltom | |
| | | | C12Q 1/6818 |
| 2002/0128465 A1 | 9/2002 | Lyamichev et al. | |
| 2002/0142454 A1 | 10/2002 | Cracauer et al. | |
| 2002/0156255 A1 | 10/2002 | Cracauer et al. | |
| 2002/0198693 A1 | 12/2002 | Marusich et al. | |
| 2003/0072689 A1 | 4/2003 | Cracauer et al. | |
| 2003/0082544 A1 | 5/2003 | Fors et al. | |
| 2003/0092039 A1 | 5/2003 | Olson-Munoz et al. | |
| 2003/0104378 A1 | 6/2003 | Allawi et al. | |
| 2003/0104470 A1 | 6/2003 | Fors et al. | |
| 2003/0113236 A1 | 6/2003 | Cracauer et al. | |
| 2003/0113237 A1 | 6/2003 | Cracauer et al. | |
| 2003/0124526 A1 | 7/2003 | Cracauer et al. | |
| 2003/0134349 A1 | 7/2003 | Ma et al. | |
| 2003/0143535 A1 | 7/2003 | Lyamichev et al. | |
| 2003/0165954 A1 | 9/2003 | Katagiri et al. | |
| 2003/0186238 A1 | 10/2003 | Allawi et al. | |
| 2003/0219784 A1 | 11/2003 | Ip et al. | |
| 2004/0014067 A1 | 1/2004 | Lyamichev et al. | |
| 2004/0018489 A1 | 1/2004 | Ma et al. | |
| 2004/0096874 A1 | 5/2004 | Neville et al. | |
| 2004/0203035 A1 | 10/2004 | Mast et al. | |
| 2004/0219576 A1 | 11/2004 | Skrzypczynski et al. | |
| 2004/0235024 A1 | 11/2004 | Lyamichev et al. | |
| 2005/0048527 A1 | 3/2005 | Allawi et al. | |
| 2005/0074788 A1 | 4/2005 | Dahlberg et al. | |
| 2005/0106596 A1 | 5/2005 | Skrzypczynski et al. | |
| 2005/0130179 A1 | 6/2005 | Lyamichev et al. | |
| 2005/0158716 A1 | 7/2005 | Dahlberg et al. | |
| 2005/0164177 A1 | 7/2005 | Neri et al. | |
| 2005/0181435 A1 | 8/2005 | Prudent et al. | |
| 2005/0186588 A1 | 8/2005 | Lyamichev et al. | |
| 2005/0196750 A1 | 9/2005 | Elagin et al. | |
| 2005/0277138 A1 | 12/2005 | Skrzypczynski et al. | |
| 2006/0147938 A1 | 7/2006 | Accola et al. | |
| 2006/0147955 A1 | 7/2006 | Allawi et al. | |
| 2006/0160074 A1 | 7/2006 | Dorn et al. | |
| 2006/0183207 A1 | 8/2006 | Lyamichev et al. | |
| 2006/0198709 A1 | 9/2006 | Marusich et al. | |
| 2006/0199202 A1 | 9/2006 | Lyamichev et al. | |
| 2006/0234252 A1 | 10/2006 | Andersen | |
| 2006/0240452 A1 | 10/2006 | Skrzypczynski et al. | |
| 2006/0246475 A1 | 11/2006 | Peterson et al. | |
| 2006/0252032 A1 | 11/2006 | Aslanukov et al. | |
| 2007/0049745 A1 | 3/2007 | Skrzypczynski et al. | |
| 2007/0087345 A1 | 4/2007 | Olson-Munoz et al. | |
| 2007/0111200 A1 | 5/2007 | Hudson et al. | |
| 2007/0134249 A1 | 6/2007 | Denney et al. | |
| 2007/0202517 A1 | 8/2007 | Agarwal et al. | |
| 2007/0207455 A1 | 9/2007 | Law et al. | |
| 2007/0292856 A1 | 12/2007 | Lyamichev et al. | |
| 2008/0014124 A1 | 1/2008 | Skrzypczynski et al. | |
| 2008/0015349 A1 | 1/2008 | Skrzypczynski et al. | |
| 2008/0032305 A1 | 2/2008 | Dorn et al. | |
| 2008/0071074 A1 | 3/2008 | Skrzypczynski et al. | |
| 2008/0131870 A1 | 6/2008 | Allawi et al. | |
| 2008/0131875 A1 | 6/2008 | Hall et al. | |
| 2008/0131890 A1 | 6/2008 | Allawi et al. | |
| 2008/0160524 A1 | 7/2008 | Ma et al. | |
| 2008/0176215 A1 | 7/2008 | Hudson et al. | |
| 2008/0181823 A1 | 7/2008 | Iszczyszyn et al. | |
| 2008/0182254 A1 | 7/2008 | Hall et al. | |
| 2008/0182980 A1 | 7/2008 | Skrzypczynski et al. | |
| 2008/0187919 A1 | 8/2008 | King et al. | |
| 2008/0187926 A1 | 8/2008 | Dahlberg et al. | |
| 2008/0188375 A1 | 8/2008 | Neri et al. | |
| 2008/0199936 A1 | 8/2008 | Lyamichev et al. | |
| 2008/0213767 A1 | 9/2008 | Western et al. | |
| 2008/0220425 A1 | 9/2008 | Ma et al. | |
| 2008/0226660 A1 | 9/2008 | Bryan et al. | |
| 2008/0261220 A1 | 10/2008 | Cracauer et al. | |
| 2008/0268455 A1 | 10/2008 | Hall et al. | |
| 2008/0293046 A1 | 11/2008 | Allawi et al. | |
| 2009/0029869 A1 | 1/2009 | Skrzypcznski et al. | |
| 2009/0041634 A1 | 2/2009 | Cracauer et al. | |
| 2009/0068664 A1 | 3/2009 | Lyamichev et al. | |
| 2009/0075256 A1 | 3/2009 | Lyamichev et al. | |
| 2009/0078574 A1 | 3/2009 | Lyamichev et al. | |
| 2009/0111092 A1 | 4/2009 | Elagin et al. | |
| 2009/0117576 A1 | 5/2009 | Dong et al. | |
| 2009/0142752 A1 | 6/2009 | Hall et al. | |
| 2009/0142754 A1 | 6/2009 | Allawi et al. | |
| 2009/0203018 A1 | 8/2009 | Agarwal et al. | |
| 2009/0215043 A1 | 8/2009 | Kwitek et al. | |
| 2009/0253142 A1 * | 10/2009 | Allawi | C12Q 1/6832 |
| | | | 435/6.1 |
| 2009/0299641 A1 | 12/2009 | Allawi et al. | |
| 2009/0305283 A1 | 12/2009 | Prudent et al. | |
| 2010/0152431 A1 | 6/2010 | Skrzypczynski et al. | |
| 2010/0304444 A1 * | 12/2010 | Morley | C12Q 1/686 |
| | | | 435/91.2 |
| 2016/0237480 A1 * | 8/2016 | Oldham-Haltom | |
| | | | C12Q 1/6886 |

OTHER PUBLICATIONS

Hosono, N., Chantarangsu, S., Kiyotani, K., Takata, S., Tsuchiya, Y., Mahasirimongkol, S., Chantratita, W., Mushiroda, T., Nakamura, Y. and Kubo, M., 2010. Development of new HLA-B* 3505 genotyping method using Invader assay. Pharmacogenetics and genomics, 20(10), pp. 630-633. (Year: 2010).*

Allawi, et al., "Invader plus method detects herpes simplex virus in

(56) References Cited

OTHER PUBLICATIONS cerebrospinal fluid and simultaneously differentiates types 1 and 2", J Clin Microbiol., 2006, 44:3443-7.
Applied Biosystems, "Methylation Analysis by Bisulfite Sequencing: Chemistry, Products and Protocols from Applied Biosystems", 2007, 52pgs.
Eads, et al., "MethyLight: a high-throughput assay to measure DNA methylation", Nucleic Acids Res., 2000, 28:E32, 8pgs.
Herman, et al., "Methylation-specific PCR: a novel PCR assay for methylation status of CpG islands", Proc Natl Acad Sci., 1996, 93:9821-6.
Itzkowitz, et al., "A simplified, noninvasive stool DNA test for colorectal cancer detection", Am J Gastroenterol., 2008, 103:2862-70.
Itzkowitz, et al., "Improved fecal DNA test for colorectal cancer screening", Clin Gastroenterol Hepatol., 2007, 5:111-7.
Qiagen, "EpiTect® MethyLight PCR Handbook", MethyLight PCR Kit, MethyLight PCR + ROX Vial Kit, 2008, 36pgs.
Tadokoro, et al., "Quantitation of viral load by real-time PCR-monitoring Invader reaction", J Virol Methods., 2009, 155:182-6.
Yamada, et al., "Fluorometric identification of 5-methylcytosine modification in DNA: combination of photosensitized oxidation and invasive cleavage", Bioconjug Chem., 2008, 19:20-3.
Zymo Research Corp., "EZ DNA Methylation-Gold™ Kit", Flyer, Catalog Nos. D5005 & D5006, Ver. 2.1.0, downloaded Feb. 23, 2011, 2pgs.
Zymo Research Corp., "EZ DNA Methylation-Gold™ Kit", Instructions, Catalog Nos. D5005 & D5006, Ver. 2.1.0, downloaded Feb. 23, 2011, 10pgs.
Zymo Research Corp., "EZ DNA Methylation™ Kit", Instruction Manual, Catalog Nos. D5001 & D5002, Ver. 1.2.2, downloaded Feb. 23, 2011, 10pgs.
Zymo Research Corp., "Material Safety Data Sheet", MSDS: CT Conversion Reagent, Creation Date: Apr. 28, 2003, Revision Date: May 4, 2009, 1-4.
Gomez, et al. "Werkhauser RP, Abath FG. Development of a real time polymerase chain reaction for quantitation of Schistosoma mansoni DNA", Mem Inst Oswaldo Cruz. Sep. 2006;1 01 Suppl 1 :133-6.
Hecker, et al., "High and low annealing temperatures increase both specificity and yield in touchdown and stepdown PCR", Biotechniques., 20(3):478-85, 2006.
Li, et al. "COLD-PCR: a new platform for highly improved mutation detection in cancer and genetic testing", Biochem Soc Trans. ,37(Pt 2):427-32, 2009.
Lindh, et al. "Real-time Taqman PCR targeting 14 human papilloma virus types", J Clin Virol. Dec. 2007;40(4):321-4. Epub Nov. 5, 2007.
Melo, et al. "Development of molecular approaches for the identification of transmission sites of schistosomiasis", Trans R Soc Trop Med Hyg. Nov. 2006; 1 00(11 ):1 049-55. Epub Apr. 18, 2006.
Minarovicova, et al. "A single-tube nested real-time polymerase chain reaction for sensitive contained detection of Cryptosporidium parvum", Lett Appl Microbial. Nov. 2009; 49(5):568-72. Epub Jul. 31, 2009.
Parsons, et al. "Genotypic selection methods for the direct analysis of point mutations", Mutat Res., 387(2):97-121, 1997.
Roux, et al. "One-step optimization using touchdown and stepdown PCR", Methods Mol Biol, 67:39-45, 1997.
Supplemental European Search Report for European Patent Application No. EP11841038, Document dated Apr. 4, 2014, 8 pages.
Tabone, et al. "Temperature switch PCR (TSP): Robust assay design for reliable amplification and genotyping of SNPs", BMC Genomics. Dec. 3, 2009;1 0:580.
Hosono et al., "Multiplex PCR-Based Real-Time Invader Assay (mPCR-RETINA): A Novel SNP-Based Method for Detecting Allelic Asymmetries Within Copy Number Variation Regions", Human Mutation, 2007, 0:1-8.
Layton et al., "Development fo Bacteroides 16S rRNA Gene TaqMan-Based Real-Time PCR Assays for Estimation of Total, Human, and Bovine Fecal Pollution in Water", Applied and Environmental Microbiology, Jun. 2006, 72(6): 4214-4224.
Penders et al., "Quantification of *Bifidobacterium* spp., *Escherichia coli* and Clostridium difficile in faecal samples of breast-fed and formula-fed infants by real-time PCR", FEMS Microbiology Letters, 2005, 243: 141-147.
Kearns et al., "Rapid detection of methicillin-resistant Staphylococci by multiplex PCR", Journal of Hospital Infection, 1999, 43: 33-37.
Nitsche et al., "Different Real-Time PCR Formats Compared for the Quantitative Detection of Human Cytomegalovirus DNA", Clinical Chemistry, 1999, 45(11): 1932-1937.

\* cited by examiner

SEQUENCE LISTING

<160> NUMBER OF SEQ ID NOS: 6

<210> SEQ ID NO 1
<211> LENGTH: 142
<212> TYPE: DNA
<213> ORGANISM: Artificial Sequence
<220> FEATURE:
<223> OTHER INFORMATION: amplification region for KRAS

<400> SEQUENCE: 1

-continued

```
atgactgaat ataaacttgt ggtagttgga gctggtggcg taggcaagag tgccttgacg    60
atacagctaa ttcagaatca ttttgtggac gaatatgatc caacaataga ggtaaatctt   120
gttttaatat gcatattact gg                                            142

<210> SEQ ID NO 2
<211> LENGTH: 142
<212> TYPE: DNA
<213> ORGANISM: Artificial Sequence
<220> FEATURE:
<223> OTHER INFORMATION: amplification region for KRAS

<400> SEQUENCE: 2
atgactgaat ataaacttgt ggtagttgga gctgttggcg taggcaagag tgccttgacg    60
atacagctaa ttcagaatca ttttgtggac gaatatgatc caacaataga ggtaaatctt   120
gttttaatat gcatattact gg                                            142

<210> SEQ ID NO 3
<211> LENGTH: 22
<212> TYPE: DNA
<213> ORGANISM: Artificial Sequence
<220> FEATURE:
<223> OTHER INFORMATION: Synthetic reverse primer

<400> SEQUENCE: 3
ctattgttgg atcatattcg tc                                             22

<210> SEQ ID NO 4
<211> LENGTH: 21
<212> TYPE: DNA
<213> ORGANISM: Artificial Sequence
<220> FEATURE:
<223> OTHER INFORMATION: Synthetic forward primer

<400> SEQUENCE: 4
acttgtggta gttggagctc t                                              21

<210> SEQ ID NO 5
<211> LENGTH: 21
<212> TYPE: DNA
<213> ORGANISM: Artificial Sequence
<220> FEATURE:
<223> OTHER INFORMATION: Synthetic probe
<220> FEATURE:
<221> NAME/KEY: misc_difference
<222> LOCATION: 21
<223> OTHER INFORMATION: 3'-C6 hexanediol group

<400> SEQUENCE: 5
gacgcggagt tggcgtaggc a                                              21

<210> SEQ ID NO 6
<211> LENGTH: 35
<212> TYPE: DNA
<213> ORGANISM: Artificial Sequence
<220> FEATURE:
<223> OTHER INFORMATION: Synthetic cleavable FRET cassette
<220> FEATURE:
<221> NAME/KEY: misc_difference
<222> LOCATION: 35
<223> OTHER INFORMATION: 3'-C6 hexanediol group
<220> FEATURE:
<221> NAME/KEY: misc_difference
<222> LOCATION: 1
<223> OTHER INFORMATION: 5'-FAM modified where FAM is fluorescein
<220> FEATURE:
```

```
<221> NAME/KEY: misc_difference
<222> LOCATION: 3
<223> OTHER INFORMATION: nucleotide modified with quencher

<400> SEQUENCE: 6
tctagccggt tttccggctg agactccgcg tccgt                              35
```

REAL TIME CLEAVAGE ASSAY

CROSS REFERENCE TO RELATED APPLICATIONS

The present application is a continuation of U.S. patent application Ser. No. 15/068,364, filed on Mar. 11, 2016, which is a continuation of Ser. No. 15/019,758, filed on Feb. 9, 2016, which is a continuation of U.S. patent application Ser. No. 13/720,757, filed on Dec. 19, 2012, now issued as U.S. Pat. No. 9,290,797, which is a continuation of U.S. patent application Ser. No. 12/946,737, filed on Nov. 15, 2010, now issued as U.S. Pat. No. 8,361,720, all of which are incorporated by reference in their entireties.

BACKGROUND

Several point mutations in the human genome have a direct association with a disease. For example, several germline KRAS mutations have been found to be associated with Noonan syndrome (Schubert et al. Nat. Genet. 2006 38: 331-6) and cardio-facio-cutaneous syndrome (Niihori et al. Nat. Genet. 2006 38: 294-6). Likewise, somatic KRAS mutations are found at high rates in leukemias, colorectal cancer (Burmer et al. Proc. Natl. Acad. Sci. 1989 86: 2403-7), pancreatic cancer (Almoguera et al. Cell 1988 53: 549-54) and lung cancer (Tam et al. Clin. Cancer Res. 2006 12: 1647-53). Many point mutations in the human genome have no apparent causative association with a disease.

Methods for the detection of point mutations may be used, for example, to provide a diagnostic for diseases that are associated with the point mutations.

SUMMARY

A cleavage-based real-time PCR assay method is provided. In certain embodiments, the assay method includes subjecting a reaction mixture comprising a) PCR reagents for amplifying a nucleic acid target, and b) flap cleavage reagents for performing a flap cleavage assay on the amplified nucleic acid target to two sets of thermocycling conditions. The first set of thermocycling conditions includes a set of 5-15 cycles of: i. a first temperature of at least 90° C.; ii. a second temperature in the range of 60° C. to 75° C.; iii. a third temperature in the range of 65° C. to 75° C. The second and third temperatures may be the same. The second set of thermocycling conditions includes a set of 20-50 cycles of: i. a fourth temperature of at least 90° C.; ii. a fifth temperature that is at least 10° C. lower than the second temperature; iii. a sixth temperature in the range of 65° C. to 75° C. In certain cases, no additional reagents are added to the reaction between the first and second sets of cycles and, in each cycle of the second set of cycles, cleavage of a flap probe is measured.

DEFINITIONS

Figure 1:
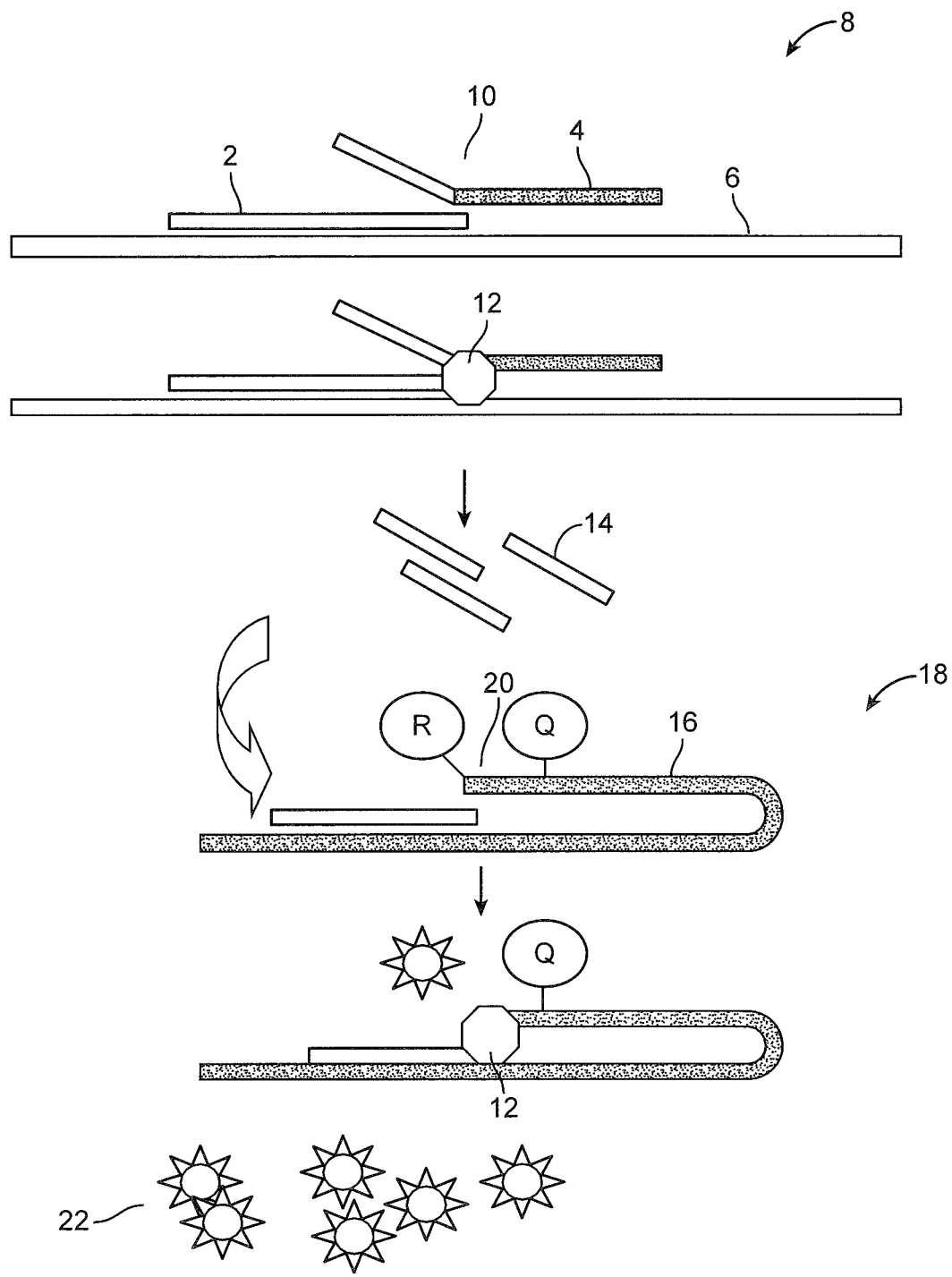
FIG. 1 schematically illustrates some of the general principles of a flap assay.

The term "sample" as used herein relates to a material or mixture of materials, typically, although not necessarily, in liquid form, containing one or more analytes of interest.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than about 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively).

The term "nucleic acid sample," as used herein denotes a sample containing nucleic acid.

The term "target polynucleotide," as used herein, refers to a polynucleotide of interest under study. In certain embodiments, a target polynucleotide contains one or more target sites that are of interest under study.

The term "oligonucleotide" as used herein denotes a single stranded multimer of nucleotides of about 2 to 200 nucleotides. Oligonucleotides may be synthetic or may be made enzymatically, and, in some embodiments, are 10 to 50 nucleotides in length.

Oligonucleotides may contain ribonucleotide monomers (i.e., may be oligoribonucleotides) or deoxyribonucleotide monomers. An oligonucleotide may be 10 to 20, 11 to 30, 31 to 40, 41 to 50, 51 to 60, 61 to 70, 71 to 80, 80 to 100, 100 to 150 or 150 to 200 nucleotides in length, for example. The term "duplex," or "duplexed," as used herein, describes two complementary polynucleotides that are base-paired, i.e., hybridized together.

The term "primer" as used herein refers to an oligonucleotide that has a nucleotide sequence that is complementary to a region of a target polynucleotide. A primer binds to the complementary region and is extended, using the target nucleic acid as the template, under primer extension conditions. A primer may be in the range of about 15 to about 50 nucleotides although primers outside of this length may be used. A primer can be extended from its 3' end by the action of a polymerase. An oligonucleotide that cannot be extended from it 3' end by the action of a polymerase is not a primer.

The term "extending" as used herein refers to any addition of one or more nucleotides to the end of a nucleic acid, e.g. by ligation of an oligonucleotide or by using a polymerase.

The term "amplifying" as used herein refers to generating one or more copies of a target nucleic acid, using the target nucleic acid as a template.

The term "denaturing," as used herein, refers to the separation of a nucleic acid duplex into two single strands.

The terms "determining", "measuring", "evaluating", "assessing," "assaying," "detecting," and "analyzing" are used interchangeably herein to refer to any form of measurement, and include determining if an element is present or not. These terms include both quantitative and/or qualitative determinations. Assessing may be relative or absolute.

"Assessing the presence of" includes determining the amount of something present, as well as determining whether it is present or absent.

The term "using" has its conventional meaning, and, as such, means employing, e.g., putting into service, a method or composition to attain an end. As used herein, the term "$T_m$" refers to the melting temperature of an oligonucleotide duplex at which half of the duplexes remain hybridized and half of the duplexes dissociate into single strands. The $T_m$ of an oligonucleotide duplex may be experimentally determined or predicted using the following formula $T_m$=81.5+ 16.6($\log_{10}$[Na$^+$])+0.41 (fraction G+C)−(60/N), where N is the chain length and [Na$^+$] is less than 1 M. See Sambrook and Russell (2001; Molecular Cloning: A Laboratory Manual, 3$^{rd}$ ed., Cold Spring Harbor Press, Cold Spring Harbor N.Y., ch. 10). Other formulas for predicting $T_m$ of oligonucleotide duplexes exist and one formula may be more or less appropriate for a given condition or set of conditions.

As used herein, the term "$T_m$-matched" refers to a plurality of nucleic acid duplexes having $T_m$s that are within a defined range, e.g., within 5° C. or 10° C. of each other.

As used herein, the term "reaction mixture" refers to a mixture of reagents that are capable of reacting together to produce a product in appropriate external conditions over a period of time. A reaction mixture may contain PCR reagents and flap cleavage reagents, for example, the recipes for which are independently known in the art.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution, or a number of different elements attached to a solid support at random or in no particular order in which the different elements are not spacially distinct. A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

As used herein, the term "PCR reagents" refers to all reagents that are required for performing a polymerase chain reaction (PCR) on a template. As is known in the art, PCR reagents essentially include a first primer, a second primer, a thermostable polymerase, and nucleotides. Depending on the polymerase used, ions (e.g., Mg$^{2+}$) may also be present. PCR reagents may optionally contain a template from which a target sequence can be amplified.

As used herein, the term "flap assay" refers to an assay in which a flap oligonucleotide is cleaved in an overlap-dependent manner by a flap endonuclease to release a flap that is then detected. The principles of flap assays are well known and described in, e.g., Lyamichev et al. (Nat. Biotechnol. 1999 17:292-296), Ryan et al (Mol. Diagn. 1999 4:135-44) and Allawi et al (J. Clin. Microbiol. 2006 44: 3443-3447). For the sake of clarity, certain reagents that are employed in a flap assay are described below. The principles of a flap assay are illustrated in FIG. 1. In the flap assay shown in FIG. 1, an invasive oligonucleotide 2 and flap oligonucleotide 4 are hybridized to target 6 to produce a first complex 8 that contains a nucleotide overlap at position 10. First complex 8 is a substrate for flap endonuclease. Flap endonuclease 12 cleaves flap oligonucleotide 4 to release a flap 14 that hybridizes with FRET cassette 16 that contains a quencher "Q" and a nearby quenched flourophore "R" that is quenched by the quencher Q. Hybridization of flap 14 to FRET cassette 16 results in a second complex 18 that contains a nucleotide overlap at position 20. The second complex is also a substrate for flap endonuclease. Cleavage of FRET cassette 16 by flap endonuclease 12 results in release of the fluorophore 22, which produces a fluorescent signal. These components are described in greater detail below.

As used herein, the term "invasive oligonucleotide" refers to an oligonucleotide that is complementary to a region in a target nucleic acid. The 3' terminal nucleotide of the invasive oligonucleotide may or may not base pair a nucleotide in the target (e.g., which may be the site of a SNP or a mutation, for example).

As used herein, the term "flap oligonucleotide" refers to an oligonucleotide that contains a flap region and a region that is complementary to a region in the target nucleic acid. The target complementary regions on the invasive oligonucleotide and the flap oligonucleotide overlap by a single nucleotide. As is known, if the 3' terminal nucleotide of the invasive nucleotide and the nucleotide that overlaps that nucleotide in the flap oligonucleotide both base pair with a nucleotide in the target nucleic acid, then a particular structure is formed. This structure is a substrate for an enzyme, defined below as a flap endonuclease, that cleaves the flap from the target complementary region of the flap oligonucleotide. If the 3' terminal nucleotide of the invasive oligonucleotide does not base pair with a nucleotide in the target nucleic acid, or if the overlap nucleotide in the flap oligonucleotide does not base pair with a nucleotide in the target nucleic acid, the complex is not a substrate for the enzyme and there is little or no cleavage.

The term "flap endonuclease" or "FEN" for short, as used herein, refers to a class of nucleolytic enzymes that act as structure specific endonucleases on DNA structures with a duplex containing a single stranded 5' overhang, or flap, on one of the strands that is displaced by another strand of nucleic acid, i.e., such that there are overlapping nucleotides at the junction between the single and double-stranded DNA. FENs catalyze hydrolytic cleavage of the phosphodiester bond at the junction of single and double stranded DNA, releasing the overhang, or the flap. Flap endonucleases are reviewed by Ceska and Savers (*Trends Biochem. Sci.* 1998 23:331-336) and Liu et al (*Annu. Rev. Biochem.* 2004 73: 589-615). FENs may be individual enzymes, multi-subunit enzymes, or may exist as an activity of another enzyme or protein complex, e.g., a DNA polymerase. A flap endonuclease may be thermostable. As used herein, the term "cleaved flap" refers to a single-stranded oligonucleotide that is a cleavage product of a flap assay.

As used herein, the term "FRET cassette" refers to a hairpin oligonucleotide that contains a fluorophore moiety and a nearby quencher moiety that quenches the fluorophore. Hybridization of a cleaved flap with a FRET cassette produces a secondary substrate for the flap endonuclease. Once this substrate is formed, the 5' fluorophore-containing base is cleaved from the cassette, thereby generating a fluorescence signal.

As used herein, the term "flap assay reagents" refers to all reagents that are required for performing a flap assay on a substrate. As is known in the art, flap assays include an invasive oligonucleotide, a flap oligonucleotide, a flap endonuclease and a FRET cassette, as described above. Flap assay reagents may optionally contain a target to which the invasive oligonucleotide and flap oligonucleotide bind.

DESCRIPTION OF EXEMPLARY EMBODIMENTS

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Described herein is a cleavage-based real-time PCR assay method. In general terms, the assay method includes subjecting a reaction mixture comprising a) PCR reagents for amplifying a nucleic acid target, and b) flap cleavage reagents for performing a flap cleavage assay on the amplified nucleic acid target to two sets of thermocycling conditions. In certain cases, no additional reagents are added to the reaction between the first and second sets of cycles and, in each cycle of the second set of cycles, cleavage of a flap probe is measured. In further describing the method, the reagent mixture used in the method will be described first, followed by a description of the thermocycling conditions used in the method.

In the following description, the skilled artisan will understand that any of a number of polymerases and flap endonucleases could be used in the methods, including without limitation, those isolated from thermostable or hyperthermostable prokaryotic, eukaryotic, or archaeal organisms. The skilled artisan will also understand that the enzymes that are used in the method, e.g., polymerase and flap endonuclease, include not only naturally occurring enzymes, but also recombinant enzymes that include enzymatically active fragments, cleavage products, mutants, and variants of wild type enzymes.

Reaction Mixture

As noted above, the reaction mixture used in the method contains at least PCR reagents for amplifying a nucleic acid target and flap cleavage reagents for performing a flap cleavage assay on the amplified nucleic acid. The reaction mixture employed in the method may therefore contain a pair of primers as well a reaction buffer (which can be pH buffered and may include salt, e.g., $MgCl_2$ and other components necessary for PCR), nucleotides, e.g., dGTP, dATP, dTTP and dCTP and a thermostable DNA polymerase, as well as a flap oligonucleotide, a flap endonuclease and a FRET cassette, as defined above. Depending on how the assay is performed (i.e., depending on whether one of the PCR primers is used as an invasive oligonucleotide in the flap assay) the reaction mix may additionally contain an invasive oligonucleotide that is distinct from the PCR primers. The reaction mixture may further contain a nucleic acid target.

The exact identities and concentrations of the reagents present in the reaction mixture may be similar to or the same as those independently employed in PCR and flap cleavage assays, with the exception that the reaction mixture contains $Mg^{2+}$ at a concentration that is higher then employed in conventional PCR reaction mixtures (which contain $Mg^{2+}$ at a concentration of between about 1.8 mM and 3 mM). In certain embodiments, the reaction mixture described herein contains $Mg^{2+}$ at a concentration in the range of 4 mM to 10 mM, e.g., 6 mM to 9 mM. Exemplary reaction buffers and DNA polymerases that may be employed in the subject reaction mixture include those described in various publications (e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). Reaction buffers and DNA polymerases suitable for PCR may be purchased from a variety of suppliers, e.g., Invitrogen (Carlsbad, Calif.), Qiagen (Valencia, Calif.) and Stratagene (La Jolla, Calif.).

Exemplary polymerases include Taq, Pfu, Pwo, UlTma and Vent, although many other polymerases may be employed in certain embodiments. Guidance for the reaction components suitable for use with a polymerase as well as suitable conditions for their use, is found in the literature supplied with the polymerase. Primer design is described in a variety of publications, e.g., Diffenbach and Dveksler (PCR Primer, A Laboratory Manual, Cold Spring Harbor Press 1995); R. Rapley, (The Nucleic Acid Protocols Handbook (2000), Humana Press, Totowa, N.J.); Schena and Kwok et al., Nucl. Acid Res. 1990 18:999-1005). Primer and probe design software programs are also commercially available, including without limitation, Primer Detective (ClonTech, Palo Alto, Calif.), Lasergene, (DNASTAR, Inc., Madison, Wis.); and Oligo software (National Biosciences, Inc., Plymouth, Minn.) and iOligo (Caesar Software, Portsmouth, N.H.).

Exemplary flap cleavage assay reagents are found in Lyamichev et al. (Nat. Biotechnol. 1999 17:292-296), Ryan et al (Mol. Diagn. 1999 4:135-44) and Allawi et al (J. Clin Microbiol. 2006 44: 3443-3447). Appropriate conditions for flap endonuclease reactions are either known or can be readily determined using methods known in the art (see, e.g., Kaiser et al., J. Biol. Chem. 274:21387-94, 1999). Exemplary flap endonucleases that may be used the method include, without limitation, Thermus aquaticus DNA polymerase I, *Thermus thermophilus* DNA polymerase I, mammalian FEN-1, *Archaeoglobus fulgidus* FEN-1, *Methanococcus jannaschii* FEN-1, *Pyrococcus furiosus* FEN-1, *Methanobacterium thermoautotrophicum* FEN-1, *Thermus thermophilus* FEN-1, CLEAVASE™ (Third Wave, Inc., Madison, Wis.), *S. cerevisiae* RTH1, *S. cerevisiae* RAD27, *Schizosaccharomyces pombe* rad2, bacteriophage T5 5'-3' exonuclease, *Pyroccus horikoshii* FEN-1, human exonuclease 1, calf thymus 5'-3' exonuclease, including homologs thereof in eubacteria, eukaryotes, and archaea, such as members of the class II family of structure-specific enzymes, as well as enzymatically active mutants or variants thereof. Descriptions of cleaving enzymes can be found in, among other places, Lyamichev et al., Science 260:778-83, 1993; Eis et al., Nat. Biotechnol. 19:673-76, 2001; Shen et al., Trends in Bio. Sci. 23:171-73, 1998; Kaiser et al. J. Biol. Chem. 274:21387-94, 1999; Ma et al., J. Biol. Chem. 275:24693-700, 2000; Allawi et al., J. Mol. Biol. 328:537-54, 2003; Sharma et al., J. Biol. Chem. 278:23487-96, 2003; and Feng et al., Nat. Struct. Mol. Biol. 11:450-56, 2004.

In particular embodiments, the reaction mix may contain reagents for assaying multiple (e.g., at least 2, 3, 4 or more) different targets sequences in parallel. In these cases, the reaction mix may contain multiple pairs of PCR primers, multiple different flap oligonucleotides having different flaps, and multiple different FRET cassettes for detecting the different flaps, once they are cleaved. In one embodiment, oligonucleotides in a mixture may have common flaps but different binding sequences to allow for, for example, a set of mutations to cleave a common FRET cassette and report a signal where a single fluorophore is indicative of the presence of a mutation. In this embodiment, which mutation is present in the sample may be determined after the presence of a mutation has identified. Optionally, the reaction may contain multiple invasive oligonucleotides if one of the PCR primers is not used as an invasive oligonucleotide. Upon cleavage of the FRET cassettes, multiple distinguishable fluorescent signals may be observed. The fluorophore may be selected from, e.g., 6-carboxyfluorescein (FAM), which has excitation and emission wavelengths of 485 nm and 520 nm respectively, Redmond Red, which has excitation and emission wavelengths of 578 nm and 650 nm respectively and Yakima Yellow, which has excitation and emission wavelengths of 532 nm and 569 nm respectively, and Quasor670 which has excitation and emission wavelengths of 644 nm and 670 nm respectively, although many others could be employed. In certain cases, at least one of the PCR primer pairs, flap oligonucleotides and FRET cassettes may be for the detection of an internal control.

As would be apparent, the various oligonucleotides used in the method are designed so as to not interfere with each other. For example, in particular embodiments, the flap oligonucleotide may be capped at its 3' end, thereby preventing its extension. Likewise, in certain embodiments, the invasive oligonucleotide may also be capped at its 3' end if it is not used as one of the PCR primers. In particular embodiment, if the invasive oligonucleotide is not used as one of the PCR primers, then the invasive oligonucleotide may be present at a concentration that is in the range of 5% to 50%, e.g., 10% to 40% of the concentration of the PCR primers. Further, in certain cases, the $T_m$s of the flap portion and the target complementary regions of the flap oligonucleotide may independently be at least 10° C. lower (e.g., 10-20° C. lower) than the $T_m$s of the PCR primers, which results in a) less hybridization of the flap oligonucleotide to the target nucleic acid at higher temperatures (60° C. to 75° C.) and b) less hybridization of any cleaved clap to the FRET cassette at higher temperatures (60° C. to 75° C.). The lower fifth temperature is favorable for hybridization of the oligonucleotides used in the flap assay, and for the activity of the flap endonuclease.

In a multiplex reaction, the primers may be designed to have similar thermodynamic properties, e.g., similar $T_m$s, G/C content, hairpin stability, and in certain embodiments may all be of a similar length, e.g., from 18 to 30 nt, e.g., 20 to 25 nt in length. The other reagents used in the reaction mixture may also be $T_m$ matched.

The assay mixture may be present in a vessel, including without limitation, a tube; a multi-well plate, such as a 96-well, a 384-well, a 1536-well plate; and a microfluidic device. In certain embodiments, multiple multiplex reactions are performed in the same reaction vessel. Depending on how the reaction is performed, the reaction mixture may be of a volume of 5 µl to 200 µl, e.g., 10 µl to 100 µl, although volumes outside of this range are envisioned.

In certain embodiments, a subject reaction mix may further contain a nucleic acid sample. In particular embodiments, the sample may contain genomic DNA or an amplified version thereof (e.g., genomic DNA amplified using the methods of Lage et al, Genome Res. 2003 13: 294-307 or published patent application US20040241658, for example). In exemplary embodiments, the genomic sample may contain genomic DNA from a mammalian cell such a human, mouse, rat or monkey cell. The sample may be made from cultured cells or cells of a clinical sample, e.g., a tissue biopsy, scrape or lavage or cells of a forensic sample (i.e., cells of a sample collected at a crime scene). In particular embodiments, the genomic sample may be from a formalin fixed paraffin embedded (FFPE) sample.

In particular embodiments, the nucleic acid sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, cerebrospinal fluid, synovial fluid, urine, amniotic fluid, and semen. In particular embodiments, a sample may be obtained from a subject, e.g., a human, and it may be processed prior to use in the subject assay. For example, the nucleic acid may be extracted from the sample prior to use, methods for which are known.

For example, DNA can be extracted from stool from any number of different methods, including those described in, e.g, Coll et al (J. of Clinical Microbiology 1989 27: 2245-2248), Sidransky et al (Science 1992 256: 102-105), Villa (Gastroenterology 1996 110: 1346-1353) and Nollau (BioTechniques 1996 20: 784-788), and U.S. Pat. Nos. 5,463,782, 7,005,266, 6,303,304 and 5,741,650. Commercial DNA extraction kits for the extraction of DNA from stool include the QIAamp stool mini kit (QIAGEN, Hilden, Germany), Instagene Matrix (Bio-Rad, Hercules, Calif.), and RapidPrep Micro Genomic DNA isolation kit (Pharmacia Biotech Inc., Piscataway, N.J.), among others.

Method for Sample Analysis

In performing the subject method, the reaction mixture is generally subjected to the following thermocycling conditions: a first set of 5 to 15 (e.g., 8 to 12) cycles of: i. a first temperature of at least 90° C.; ii. a second temperature in the range of 60° C. to 75° C. (e.g., 65° C. to 75° C.); iii. a third temperature in the range of 65° C. to 75° C.; followed by: a second set of 20-50 cycles of: i. a fourth temperature of at least 90° C.; ii. a fifth temperature that is at least 10° C. lower than the second temperature (e.g., in the range of 50° C. to 55° C.; and iii. a sixth temperature in the range of 65° C. to 75° C. No additional reagents need to be added to the reaction mixture during the thermocycling, e.g., between the first and second sets of cycles. In particular embodiments, the thermostable polymerase is not inactivated between the first and second sets of conditions, thereby allowing the target to be amplified during each cycle of the second set of cycles. In particular embodiments, the second and third temperatures are the same temperature such that "two step" thermocycling conditions are performed. Each of the cycles may be independently of a duration in the range of 10 seconds to 3 minutes, although durations outside of this range are readily employed.

In each cycle of the second set of cycles (e.g., while the reaction is in the fifth temperature), a signal generated by cleavage of the flap probe may be measured to provide a real-time measurement of the amount of target nucleic acid in the sample (where the term "real-time" is intended to refer to a measurement that is taken as the reaction progresses and products accumulate). The measurement may be expressed as an absolute number of copies or a relative amount when normalized to a control nucleic acid in the sample.

Without being bound to any specific theory, it is believed that the higher reaction temperatures in the first set of cycles may allow the target nucleic acid to be efficiently amplified by the pair of PCR primers without significant interference by any of the flap assay reagents or their reaction products. The lower reaction temperature used in the second set of cycles (i.e., the fifth temperature) is not optimum for the polymerase used for PCR, but allows the flap oligonucleotide to efficiently hybridize to the target nucleic acid and is closer to the optimum temperature of the flap endonuclease. The lower reaction temperature used in the second set of cycles also facilitates subsequent hybridization of the cleaved flap to the FRET cassette. Thus, at a lower temperature, the target nucleic acid may be detected without significant interference from the PCR reagents.

In certain cases, fluorescence indicating the amount of cleaved flap can be detected by an automated fluorometer designed to perform real-time PCR having the following features: a light source for exciting the fluorophore of the FRET cassette, a system for heating and cooling reaction mixtures and a fluorometer for measuring fluorescence by the FRET cassette. This combination of features, allows real-time measurement of the cleaved flap, thereby allowing the amount of target nucleic acid in the sample to be quantified. Automated fluorometers for performing real-time PCR reactions are known in the art and can be adapted for use in this specific assay, for example, the ICYCLERTM from Bio-Rad Laboratories (Hercules, Calif.), the Mx3000P™, the MX3005P™ and the MX4000™ from Stratagene (La Jolla, Calif.), the ABI PRISM™ 7300, 7500, 7700, and 7900 Taq Man (Applied Biosystems, Foster City, Calif.), the SMARTCYCLERTM, ROTORGENE 2000™ (Corbett Research, Sydney, Australia) and the GENE XPERT™ System (Cepheid, Sunnyvale, Calif.) and the LIGHTCYCLER™ (Roche Diagnostics Corp., Indianapolis, Ind.). The speed of ramping between the different reaction temperatures is not critical and, in certain embodiments, the default ramping speeds that are preset on thermocyclers may be employed.

In certain cases, the method may further involve graphing the amount of cleavage that occurs at each of the second set of cycles, thereby providing an estimate of the abundance of the nucleic acid target. The estimate may be calculated by determining the threshold cycle (i.e., the cycle at which this fluorescence increases above a predetermined threshold; the "Ct" value or "Cp" value). This estimate can be compared to a control (which control may be assayed in the same reaction mix as the genomic locus of interest) to provide a normalized estimate. The thermocycler may also contain a software application for determining the threshold cycle for each of the samples. An exemplary method for determining the threshold cycle is set forth in, e.g., Luu-The et al (Biotechniques 2005 38: 287-293).

A device for performing sample analysis is also provided. In certain embodiments, the device comprises: a) a thermocycler programmed to perform the above-described and b) a vessel comprising: PCR reagents for amplifying a nucleic acid target, and flap cleavage reagents for performing a flap cleavage assay on the nucleic acid target.

Utility

The method described finds use in a variety of applications, where such applications generally include sample analysis applications in which the presence of a target nucleic acid sequence in a given sample is detected.

In particular, the above-described methods may be employed to diagnose, to predict a response to treatment, or to investigate a cancerous condition or another mammalian disease, including but not limited to, leukemia, breast carcinoma, prostate cancer, Alzheimer's disease, Parkinsons's disease, epilepsy, amylotrophic lateral schlerosis, multiple sclerosis, stroke, autism, mental retardation, and developmental disorders. Many nucleotide polymorphisms are associated with and are thought to be a factor in producing these disorders. Knowing the type and the location of the nucleotide polymorphism may greatly aid the diagnosis, prognosis, and understanding of various mammalian diseases. In addition, the assay conditions described herein can be employed in other nucleic acid detection applications including, for example, for the detection of infectious diseases, viral load monitoring, viral genotyping, environmental testing, food testing, forensics, epidemiology, and other areas where specific nucleic acid sequence detection is of use.

In some embodiments, a biological sample may be obtained from a patient, and the sample may be analyzed using the method. In particular embodiments, the method may be employed to identify and/or estimate the amount of mutant copies of a genomic locus that are in a biological sample that contains both wild type copies of a genomic locus and mutant copies of the genomic locus that have a point mutation relative to the wild type copies of the genomic locus. In this example, the sample may contain at least 100 times (e.g., at least 1,000 times, at least 5,000 times, at least 10,000 times, at least 50,000 times or at least 100,000 times) more wild type copies of the genomic locus than mutant copies said genomic locus.

In these embodiments, the method may be employed to detect an oncogenic mutation (which may be a somatic mutation) in, e.g., PIK3CA, NRAS, KRAS, JAK2, HRAS, FGFR3, FGFR1, EGFR, CDK4, BRAF, RET, PGDFRA, KIT or ERBB2, which mutation may be associated with breast cancer, melanoma, renal cancer, endometrial cancer, ovarian cancer, pancreatic cancer, leukemia, colorectal cancer, prostate cancer, mesothelioma, glioma, meullobastoma, polythemia, lymphoma, sarcoma or multiple myeloma (see, e.g., Chial 2008 Proto-oncogenes to oncogenes to cancer. Nature Education 1:1).

In these embodiments, the reaction mixture may contain a first primer and a second primer wherein the first primer comprises a 3' terminal nucleotide that base pairs with the point mutation. The first primer may be employed as the invasive oligonucleotide in the second set of cycles or, in certain cases, there may be a separate invasive oligonucleotide present in the reaction mixture that also has a 3' terminal nucleotide that base pairs with the point mutation. Since the point mutation in the genomic locus may have a direct association with cancer, e.g., colorectal cancer, the subject method may be employed to diagnose patients with cancer, alone, or in combination with other clinical techniques (e.g., a physical examination such as a colonoscopy or immunohistochemical analysis) or molecular techniques. For example, results obtained from the subject assay may be combined with other information, e.g., information regarding the methylation status of other loci, information regarding in the same locus or at a different locus, cytogenetic information, information regarding rearrangements, gene expression information or information about the length of telemerers, to provide an overall diagnosis of cancer or other diseases.

In one embodiment, a sample may be collected from a patient at a first location, e.g., in a clinical setting such as in a hospital or at a doctor's office, and the sample may forwarded to a second location, e.g., a laboratory where it is processed and the above-described method is performed to generate a report. A "report" as described herein, is an electronic or tangible document which includes report elements that provide test results that may include a Ct or Cp value or the like that indicates the presence of mutant copies of the genomic locus in the sample. Once generated, the report may be forwarded to another location (which may the same location as the first location), where it may be interpreted by a health professional (e.g., a clinician, a laboratory technician, or a physician such as an oncologist, surgeon, pathologist), as part of a clinical diagnosis.

Kits

Also provided are kits for practicing the subject method, as described above. The components of the kit may be present in separate containers, or multiple components may be present in a single container.

In addition to above-mentioned components, the kit may further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In addition to the instructions, the kits may also include one or more control samples, e.g., positive or negative controls analytes for use in testing the kit.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

EXAMPLE 1

KRAS G35T Assay

The assay described below is designed to detect nucleic acid sequences containing the KRAS G35T mutation in a background of wild type sequences. For reference, partial nucleotide sequences for the wild type and G35T mutant alleles of KRAS are shown below.

Partial sequence of amplification region for KRAS, wild type (position 35 underlined):

(SEQ ID NO: 1)
ATGACTGAATATAAACTTGTGGTAGTTGGAGCTG<u>G</u>TGGCGTAGGCAAGAG

TGCCTTGACGATACAGCTAATTCAGAATCATTTTGTGGACGAATATGATC

CAACAATAGAGGTAAATCTTGTTTTAATATGCATATTACTGG

Partial sequence of amplification region for KRAS, mutant G35T (position 35 underlined):

(SEQ ID NO: 2)
ATGACTGAATATAAACTTGTGGTAGTTGGAGCTG<u>T</u>TGGCGTAGGCAAGAG

TGCCTTGACGATACAGCTAATTCAGAATCATTTTGTGGACGAATATGATC

CAACAATAGAGGTAAATCTTGTTTTAATATGCATATTACTGG

The ability to detect the KRAS mutation T at position 35 in a background of wild type G at position 35 was tested using two different thermocycling protocols, one of which uses single stage cycling and the other uses two stage cycling (see Table 1). In both protocols, at all dilutions, approximately 100,000 copies (i.e., 100,000 double stranded plasmids) of the wild type sequence were present. To the 100,000 copies of wild type, approximately 10,000, 1000, 100, and 10 copies of the mutant target gene were added. A sample containing 100,000 copies of the mutant sequence was used as a control.

Table 1 summarizes the cycling conditions for the cleavage-based assay for single stage thermocycling and two stage thermocycling. Fluorescent signal acquisition occurs at the 53° C. temperature, conducive to the cleavage reaction of the flap probe from the target and the cleavage of the fluorophore from the FRET cassette as mediated by the released flap.

TABLE 1

Single Stage Cycling Compared to 2-Stage (Headstart) Protocol

| Stage | Temperature | Time | Single Stage: Number of Cycles | 2-Stage (Headstart): Number of Cycles | Fluorescent Signal Acquisition |
|---|---|---|---|---|---|
| Pre-incubation (enzyme activation) | 95° C. | 2 min. | 1 | 1 | None |
| Amplification (Pre-Amp, Headstart) | 95° C. | 20 sec. | NONE | 10 | None |
| | 67° C. | 30 sec. | | | None |
| | 70° C. | 30 sec. | | | None |
| Amplification | 95° C. | 20 sec | 50 | 45 | None |
| | 53° C. | 1 min. | | | Single |
| | 70° C. | 30 sec. | | | None |
| Cooling (Hold) | 40° C. | 30 sec. | 1 | 1 | None |

Primers for the PCR amplification of the KRAS G35T mutation were 5'-CTATTGT TGGATCATATTCGTC-3' (SEQ ID NO:3) as the reverse primer and 5'-ACTTGTGGTAGT TGGAGCTC<u>T</u>-3' (SEQ ID NO:4) as the forward primer. Note that in the forward primer, the 3'T base (underlined) corresponds to the mutant position 35. The penultimate C at position 34 is also a mismatch to both the mutant and wild type sequence, and is designed to increase the discrimination of the 3' base against the wild type target.

The homogeneous detection of the KRAS G35T mutation was accomplished by the use of an endonuclease cleavable flap probe, a cleavable FRET cassette, and a heat stable flap endonuclease. For the detection of the G35T mutation, the flap probe sequence was 5'-GACGCGGAG TTGGCG<u>T</u>AGGCA-3'/3C6 (SEQ ID NO:5), where the mutant base is shown underlined and the 3'-end is blocked with a hexanediol group in order to inhibit extension. The cleaved flap portion, which subsequently binds the FRET cassette, and in turn releases the fluorophore away from its quencher, includes all of the bases from the 5'-end to the mutation-specific T. Primers and flap probes were supplied as non-catalog items by Integrated DNA Technologies (IDT, Coralville, Iowa).

The FRET cassette used was 5'-FAM/TCT/Quencher/ AGCCGGTTTTCCGGCT GAGACTCCGCGTCCGT-3'/ 3C6 (SEQ ID NO:6), where FAM is fluorescein, the quencher is the Eclipse® Dark Quencher, and the 3'-end is blocked with a hexanediol group in order to inhibit primer extension. The FRET cassette was supplied by Hologic (Madison, Wis.).

The PCR reactions were done in LightCycler® 480 Multiwell 96 Plates (Roche, Indianapolis) in 10 mM MOPS pH 7.5, with 7.5 mM $MgCl_2$, and 250 µM dNTPs (Promega, Madison, Wis.). Taq polymerase was the iTaq enzyme (BioRad, Hercules, Calif.) and the cleavage enzyme was Cleavase 2.0 (Hologic, Madison, Wis.). Forward primer concentration was 50 nM, reverse primer concentration was 500 nM, flap probe was at 500 nM, and the FRET cassette was used at a final concentration of 200 nM. All amplification and detection was performed in the LightCycler 480 optical thermocycler (Roche, Indianapolis, Ind.).

Figure 2:
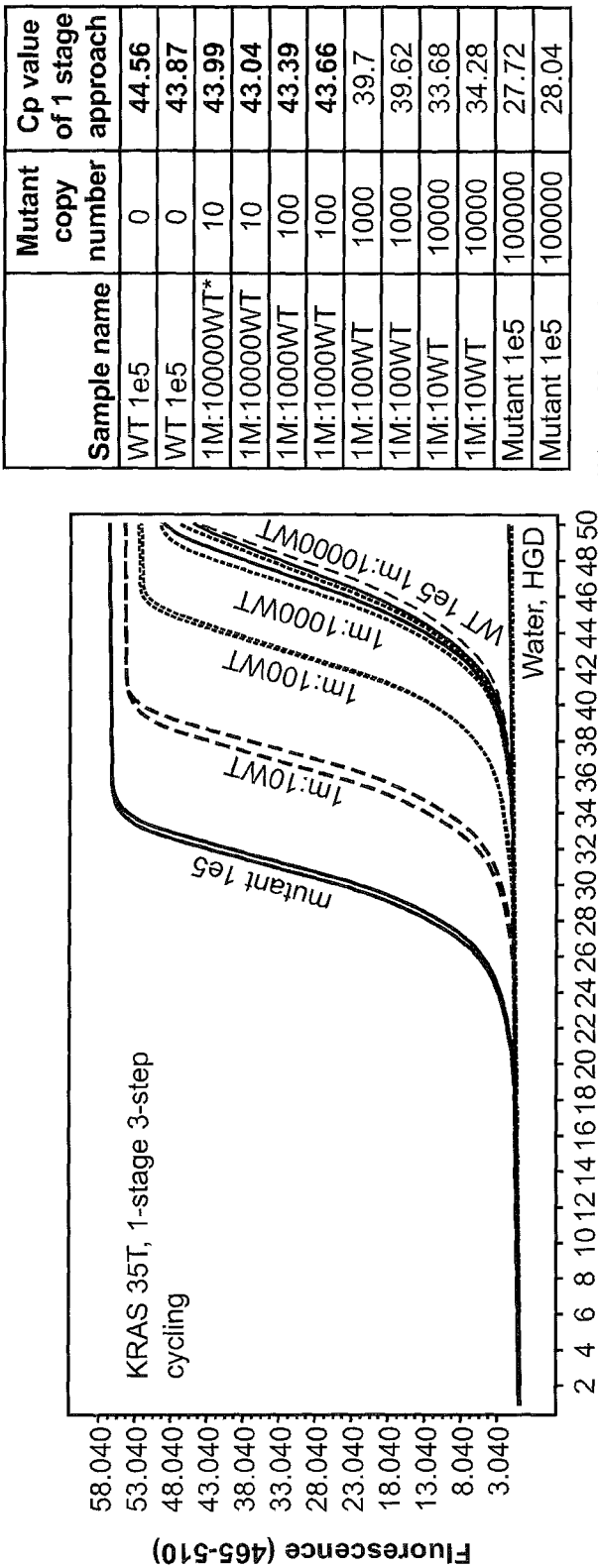
FIG. 2 shows results of an assay done using single stage thermocycling. Detection and quantitation of the KRAS G35T mutation in the presence of the wild type sequence at levels, as indicated. Kinetic curves show all ratios of mutant to wild type other than 1:10 and 1:100 are indistinguishable.
Figure 3:
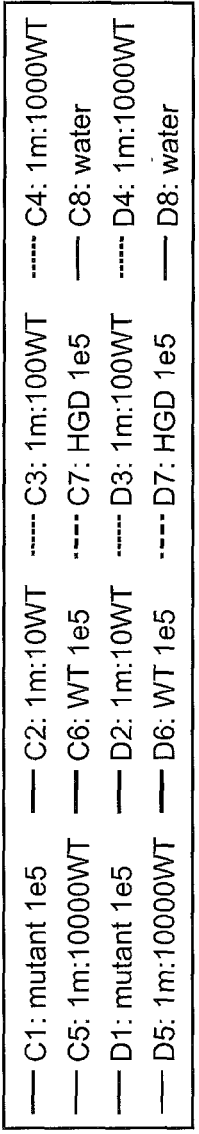
FIG. 3 shows results of an assay done using two stage thermocycling. Detection and quantitation of the KRAS G35T mutation in the presence of the wild type sequence at levels, as indicated. Kinetic curves show resolution of ratios from 1:10 to 1:10,000.
Figure 3:
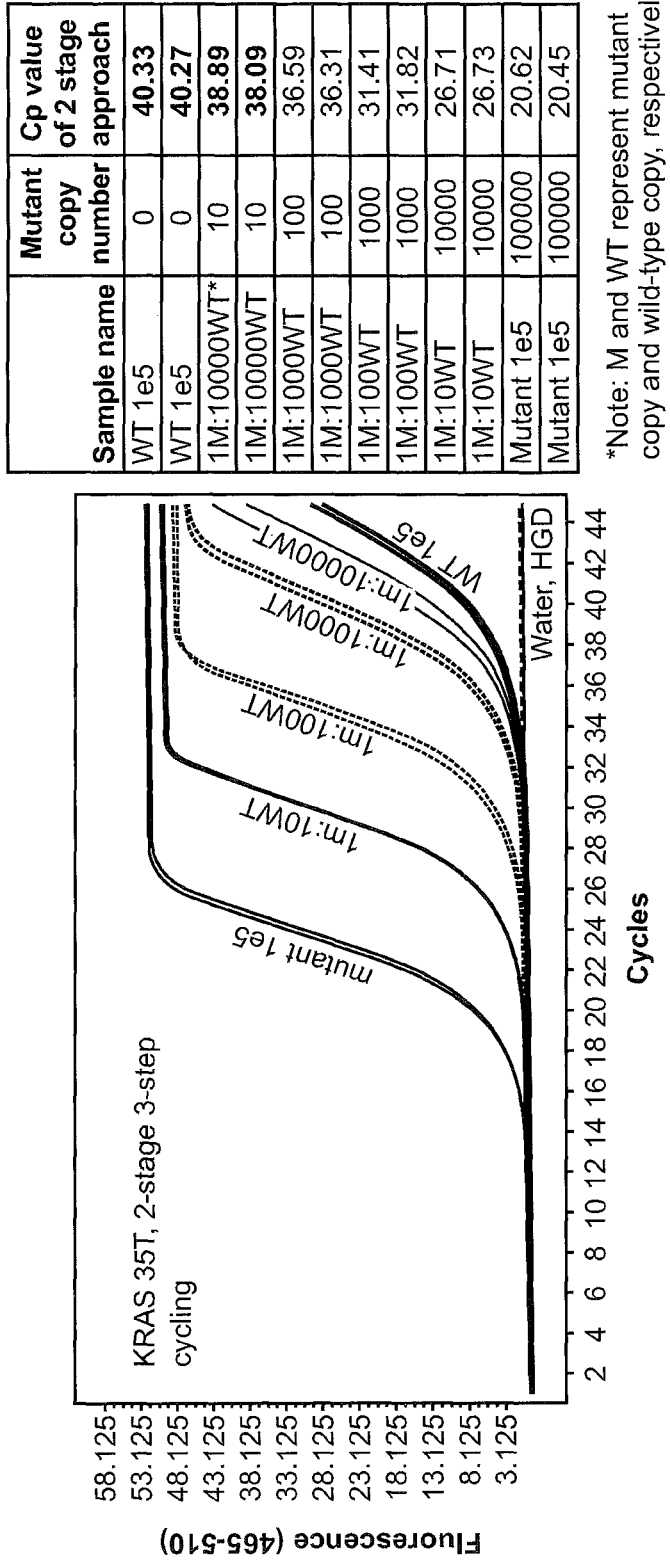

Raw data and kinetic curves, as generated by the LightCycler, for the two different cycling conditions, as summarized in Table 1, are shown in FIGS. 2 and 3. The results, showing the improved linear quantitative response of the 2-stage cycling protocol are delineated in Table 2.

Table 2 shows the detection and quantitation of the KRAS G35T mutation in the presence of the wild type sequence at levels, as indicated, comparing two different cycling protocols. The point at which the fluorescence of a sample rises above the background fluorescence is called the "crossing point (Cp)" of the sample (Roche LightCycler 480 Manual, Indianapolis, Ind.), and in these assays is calculated as being the point at which fluorescence rose to 18% of the maximum fluorescence. Cp levels above 40 cycles show no detectable dose response.

TABLE 2 detection and quantitation of the KRAS G35T mutation

| Mutant 35T copies | Wild Type 35G copies | Ratio of Mutant:Wild Type | 1-Stage Crossing Point (Cp) | 2-Stage (Headstart) Crossing Point (Cp) |
|---|---|---|---|---|
| 0 | 100000 | N/A | 44.56 | 40.33 |
| 0 | 100000 | N/A | 43.87 | 40.27 |
| 10 | 99990 | 1:10000 | 43.99 | 38.89 |
| 10 | 99990 | 1:10000 | 43.04 | 38.09 |
| 100 | 99900 | 1:1000 | 43.39 | 36.59 |
| 100 | 99900 | 1:1000 | 43.66 | 36.31 |
| 1000 | 99000 | 1:100 | 43.66 | 31.41 |
| 1000 | 99000 | 1:100 | 39.70 | 31.82 |
| 10000 | 90000 | 1:10 | 39.62 | 26.71 |
| 10000 | 90000 | 1:10 | 33.68 | 26.73 |
| 100000 | 0 | N/A | 27.72 | 20.62 |
| 100000 | 0 | N/A | 28.04 | 20.45 |

What is claimed is:

1. A method for detecting a target nucleic acid, comprising:
(a) subjecting a PCR reaction mixture comprising a flap endonuclease activity to thermocycling conditions that comprise:
i. a first set of 5 to 15 cycles each comprising a denaturation step followed by one or more steps in which all temperatures are in the range of 60° C. to 75° C.; followed by:
ii. a second set of 20 to 50 cycles each comprising a denaturation step followed by one or more steps comprising a temperature that is in the range of 50° C. to 57° C.;
wherein the PCR reaction mixture comprises at least a first set of PCR primers, wherein the first set of PCR primers consists of a single pair of PCR primers that bind to sites that flank the target nucleic acid and wherein the target nucleic acid is amplified by the first set of PCR primers and not any other primers that may be present in the PCR reaction mixture; and
(b) detecting a fluorescent signal in at least some cycles of the second set, wherein the fluorescent signal is generated by cleavage of a probe by the flap endonuclease activity and indicates the presence of a target nucleic acid
wherein no additional reagents are added to the PCR reaction mixture between said first and second sets.

2. The method of claim 1, wherein the cycles of the second set of 20 to 50 cycles each comprises a temperature that is in the range of 50° C. to 55° C.

3. The method of claim 1, wherein the measuring step of (b) comprises measuring cleavage of a fluorophore from an oligonucleotide in each of the second set of 20 to 50 cycles.

4. The method of claim 1, wherein the fluorescent signal of (b) indicates a mutation.

5. The method of claim 1, wherein step (a) comprises an initial pre-incubation step that activates a thermostable polymerase.

6. The method of claim 1, wherein the method further comprises graphing the amount of fluorescent signal that is detected in each of the 20-50 cycles, thereby providing an estimate of the abundance of the target nucleic acid in the reaction mix.

7. The method of claim 1, wherein step (b) comprises measuring two fluorescent signals in at least some of cycles of the second set, wherein the fluorescent signals respectively indicate the presence of two different mutations.

8. A method for detecting a target nucleic acid comprising:
(a) subjecting a PCR reaction mixture comprising a flap endonuclease activity to thermocycling conditions that comprise:
i. a first set of 5 to 15 cycles each comprising a denaturation step followed by one or more steps in which all temperatures are in the range of 65° C. to 75° C.; followed by
ii. a second set of 20 to 50 cycles each comprising a denaturation step followed by one or more steps comprising a temperature that is in the range of 50° C. to 65° C.,
wherein the PCR reaction mixture comprises at least a first set of PCR primers, wherein the first set of PCR primers consists of a single pair of PCR primers that bind to sites that flank the target nucleic acid and wherein the target nucleic acid is amplified by the first set of PCR primers and not any other primers that may be present in the PCR reaction mixture; and
(b) detecting a fluorescent signal in at least some cycles of the second set, wherein the fluorescent signal is generated by cleavage of a probe by the flap endonuclease activity and indicates the presence of a target nucleic acid, wherein no additional reagents are added to the PCR reaction mixture between said first and second sets.

9. The method of claim 8, wherein the cycles of the second set of 20 to 50 cycles each comprises a temperature that is in the range of 50° C. to 55° C.

10. The method of claim 8, wherein the measuring step of (b) comprises measuring cleavage of a fluorophore from an oligonucleotide in each of the second set of 20 to 50 cycles.

11. The method of claim 8, wherein the fluorescent signal of (b) indicates a mutation.

12. The method of claim 8, wherein step (a) comprises an initial pre-incubation step that activates a thermostable polymerase.

13. The method of claim 8, wherein the method further comprises graphing the amount of fluorescent signal that is detected in each of the 20-50 cycles, thereby providing an estimate of the abundance of the target nucleic acid in the reaction mix.

14. The method of claim 8, wherein step (b) comprises measuring two fluorescent signals in at least some of the cycles of the second set, wherein the fluorescent signals respectively indicate the presence of two different mutations.

* * * * *